United States Patent [19]
Eckfeldt et al.

[11] 3,941,665
[45] Mar. 2, 1976

[54] CATION CONCENTRATION MEASUREMENTS

[75] Inventors: Edgar L. Eckfeldt, Ambler; William E. Proctor, Norristown; James U. Eynon, Willow Grove, all of Pa.

[73] Assignee: Leeds & Northrup Company, Philadelphia, Pa.

[22] Filed: Dec. 3, 1971

[21] Appl. No.: 204,773

Related U.S. Application Data

[62] Division of Ser. No. 750,388, Aug. 5, 1968, abandoned.

[52] U.S. Cl........... 324/30 R; 204/195 R; 204/195 G
[51] Int. Cl.²........................................ G01N 27/46
[58] Field of Search............ 204/1 T, 195 R, 195 M, 204/195 L

[56] References Cited
UNITED STATES PATENTS
3,591,481  7/1971  Riseman........................ 204/195 R

*Primary Examiner*—T. Tung
*Attorney, Agent, or Firm*—Woodcock, Washburn, Kurtz & Mackiewicz

[57] ABSTRACT

In the measurement of ion concentration, a selected base is added to the sample liquid which reduces the hydrogen ion content without producing other cations of a size to which the measuring electrode is sensitive. Bases having a high molecular weight and a dissociation constant, particularly secondary and tertiary amines are suitable for us. The system includes an absorber which mixes sample liquid with gaseous base, means for pressurizing the reference electrode, and an analyzer cell which prevents contamination of the measuring electrode with reference fluid leaking from the reference electrode. A separate reservoir mixes known concentration solutions for calibration purposes. The concentration readout meter of the system includes an auxiliary dial for ease of calibration.

2 Claims, 11 Drawing Figures

CATION CONCENTRATION MEASUREMENTS

This is a divisional of application Ser. No. 750,388, filed Aug. 5, 1968, now abandoned.

BACKGROUND OF THE INVENTION

The measurement of sodium ion is of importance in several fields. In addition to important laboratory applications in chemistry and biology, the sodium ion electrode is finding acceptance in industry, particularly in water pollution and water purity applications. Power plants require very high purity water for successful operation of their generating equipment. Raw water must be extensively treated to remove impurities; and the high quality of water used in generating systems must be rigorously maintained.

Heretofore electrolytic conductivity measurements have been extensively used to monitor the quality of water in power plants. An electrolytic conductivity measurement has the limitation, however, of responding not only to the harmful impurities which operators want to detect but also to certain other substances they deliberately add to the boiler water to improve operating conditions. Recently, there has been a trend toward specific measurement of sodium ion to indicate the total impurity content of boiler water. Sodium ion is almost always present in substances that contaminate boiler water. Hence, the presence of sodium ion is a good indication of contamination, as may enter, for instance, through a leaky tube in a condenser unit.

Flame photometry has been used to measure the sodium ion content of boiler water. However, this measurement is rather difficult to make, requires trained personnel, and entails the use of complicated apparatus that is not suitable in its present state of development for continuous monitoring of plant streams. Accordingly, there has been considerable interest in attempting to adapt the sodium ion electrode to the problem.

Sodium ion analyzers of the electrode type are described in "Monitoring Sodium in High Purity Water," R. H. Jones, *Industrial Water Engineering*, Vol. 1, No. 2, March/April, 1964; and in Calgon Bulletin 5-1038-S, Sept. 1, 1965, *Equipment and Instruments*, a publication of the Calgon Corporation, Pittsburgh, Pennsylvania.

Sodium ion glass electrodes are similar to ordinary pH glass electrodes except that the composition of the glass used in the ion sensitive membrane is selected to respond primarily to the sodium ion rather than to the hydrogen ion as in the pH electrode. Whereas the pH electrode responds faithfully to hydrogen ion over an extremely wide range of concentration and almost without any interference effects, the sodium ion electrode will respond not only to sodium ion but also to hydrogen ion and to a number of other cations. By shifting the glass composition, one can modify the relative degree of response to these several cations, but thus far it has not been possible to make an electrode that is uniquely sensitive to sodium ion alone.

The discrimination capability of a sodium ion electrode is expressed by the so-called selectivity ratio, which is a measure of the extent to which the electrode will respond to two different ions in question, for example, sodium ion versus hydrogen ion, sodium ion versus potassium ion, or sodium ion versus ammonium ion. The selectivity ratio constant, K may be thought of as that factor by which the activity, or concentration, of a second ion species must be multiplied in order for the electrode to respond equally to the two species. Electrodes are usually very much more selective to hydrogen ion than to metal ions, and the K values (hydrogen/sodium) may range from 10 to 1000. Accordingly, for equal response to hydrogen ion and the metal ion, the hydrogen ion activity (concentration) must be much less than the metal ion activity value.

In some applications, the level of sodium ion may be sufficiently high that measurements can be made successfully in neutral (7pH) solutions, or even at lower pH values. In other applications, the level of sodium ion may be quite low, in which case the pH of the sample must be raised to a suitable value to eliminate effects of hydrogen ion on the measurement.

For example, in boiler water applications it is desired to measure very low levels of sodium ion, at times going down to 1/10 part per billion. This concentration corresponds to a molarity or normality of approximately $4 \times 10^{-9}$ in sodium ion. In order to measure this very low concentration of sodium, the hydrogen ion concentration must be reduced.

The prior art has accomplished this by adding a buffering agent, or base, to the sample liquid in order to reduce hydrogen ion activity. Commonly, ammonia and morpholine have been added to the sample liquid to raise the pH so that the hydrogen ion background is reduced. These prior art techniques have not been completely successful, particularly where extremely low levels of sodium ion concentration must be measured. As noted in the article "Beckman's Specific Ion Electrodes," *Beckman Analyzer*, Vol. 4 (1) 1963, page 3, the pH of the resulting solution must be raised to a value higher than 10.5. This article attributes the adverse effect on the electrode during prolonged contact to the high pH or high hydroxyl ion content of the solution.

SUMMARY OF THE INVENTION

This invention relates to methods of and means for measuring ion concentration by an electrode that is sensitive to the selected ion and more particularly to methods of measuring sodium ion concentration with a sodium ion glass electrode.

An important aspect of the present invention is based on the discovery that the deteriorating performance of ion selective electrodes when a strong base is added to the sample liquid is not caused by the adverse effect of the strong base (hydroxyl ion) on the electrode itself. Rather, poor ion selectivity is brought about by the production of secondary ions of a size to which the ion selective glass electrode is sensitive. Therefore, in accordance with this invention a high pH solution (high hydroxyl ion concentration) can be used provided the base is selected from a group which produces positive ions of sufficient size that the electrode will not respond to them.

The use of the base agents taught in the prior art produced in solution a high background of ions to which the electrode was sensitive. For example, when ammonia is used as the base, as taught in the prior art, the ammonium ion $NH_4^+$ is produced in solution. The ammonium ion is a relatively small cation similar in characteristics to the alkali metal cations. The ion selective electrode responds to ammonium ion. Because of this, ammonia cannot be mixed with the sample liquid in an amount sufficient to reduce the amount of hydrogen ions present to a suitable level.

Accordingly, it is an important object of the present invention to add to the sample liquid a base which reduces the amount of hydrogen ions present in the resulting solution to a suitable level without the formation of small cations to which an ion selective glass electrode would otherwise respond and which would otherwise obscure the measurement of selected cations.

It has been found that the production of secondary ions of a size to which the ion selective glass electrode is sensitive is primarily a function of the molecular weight of the base. In particular, a base selected from the group which has a molecular weight of at least 45 and a dissociated constant greater in magnitude that $5 \times 10^{-5}$ is particularly effective in reducing the amount of hydrogen ions present in the resulting solution without the formation of small cations to which the electrode will respond.

Even more particularly, the group of secondary and tertiary amines are used as a base to reduce the amount of hydrogen ions present in a sample liquid without forming small cations to which the ion sensitive electrode will respond. The cations of the secondary and tertiary amines are of a size such that cation sensitive glass electrodes are not particularly sensitive to them. See "Response of the Cation Sensitive Glass Electrodes to Alkali-Substituted Ammonium Ions" by G. A. Rechnitz and G. Kugler, Z. anal. Chem. Vol. 210, pages 174–6, (1965). The uses of these secondary and tertiary amines as a base in the treatment of sample liquids is an important part of the present invention.

In addition to the hydrogen ions present in the sample liquid, ammonium ions may be present in concentration several decades higher than that of the sodium ion to be measured.

Of the total ammonium ($NH_4^+$ and $NH_4OH$) present in a solution of pH 10.5, about 6 percent will be in ionized form. At a pH of 11.0, the ionized fraction drops to about 2 percent, while at pH 11.5 the ionization further diminishes to about 0.6 percent. It is not feasible to obtain the desired suppression effect with weak bases. The use of ammonia as the hydroxyl producing agent is particularly objectionable in this regard because it produces as much ammonium ion as hydroxyl ion.

Accordingly, it is another object of the present invention to add to the sample liquid a base from the group described above in a quantity sufficient to produce a pH greater than 11 and which will produce in solution undissociated ammonium hydroxide with a small ionized fraction thereby further improving the response of the analyzer to sodium ions relative to ammonium ions. It should be understood that to accomplish this it is necessary that the dissociation constant of the base be appreciably higher than that of ammonia and should be at least $5 \times 10^{-5}$.

In one particular embodiment of the invention, liquid diisopropyl amine is used as the base agent. A non-reactive gas is bubbled through the liquid amine to produce a transported vapor which is mixed with the sample liquid in an absorber. In another embodiment of the invention, gaseous dimethyl amine is the base. In accordance with another important object of the present invention, there is provided an absorber which is suitable for use with a gaseous base of the type described above, whether it be a pure gaseous base or a transported vapor formed from a mixture of liquid base and non-reactive gas.

It is a further object of the present invention to provide an ion concentration analysis system of the type which includes a reference electrode having a liquid junction wherein the system includes means for supplying a reference fluid to the liquid junction with a pressure greater than approximately 4 psi.

It is a further object of the present invention to provide an analyzer cell for a system of the type described above constructed in a manner which prevents under usual operating conditions reference fluid from reaching the ion sensitive element of the meansuring electrode.

It is a further object of the present invention to provide an analyzer cell for an ion concentration measuring system constructed in such a manner that the liquid level in the cell drops when there is an interruption in the normal flow of sample liquid to prevent contamination of the ion measuring element with reference fluid.

It is a further object of the present invention to provide calibration techniques for an ion concentration measuring system which are accurate, convenient and reliable.

It is a further object of the present invention to provide an ion concentration measuring system including a calibration reservoir for mixing a sample of known concentration and an auxiliary scale on the concentration meter providing ease of calibration.

The foregoing and other objects, features and advantages of the present invention will be more apparent from the following more detailed description and appended claims in conjunction with the drawings.

DESCRIPTION OF A PARTICULAR EMBODIMENT

Figure 1:
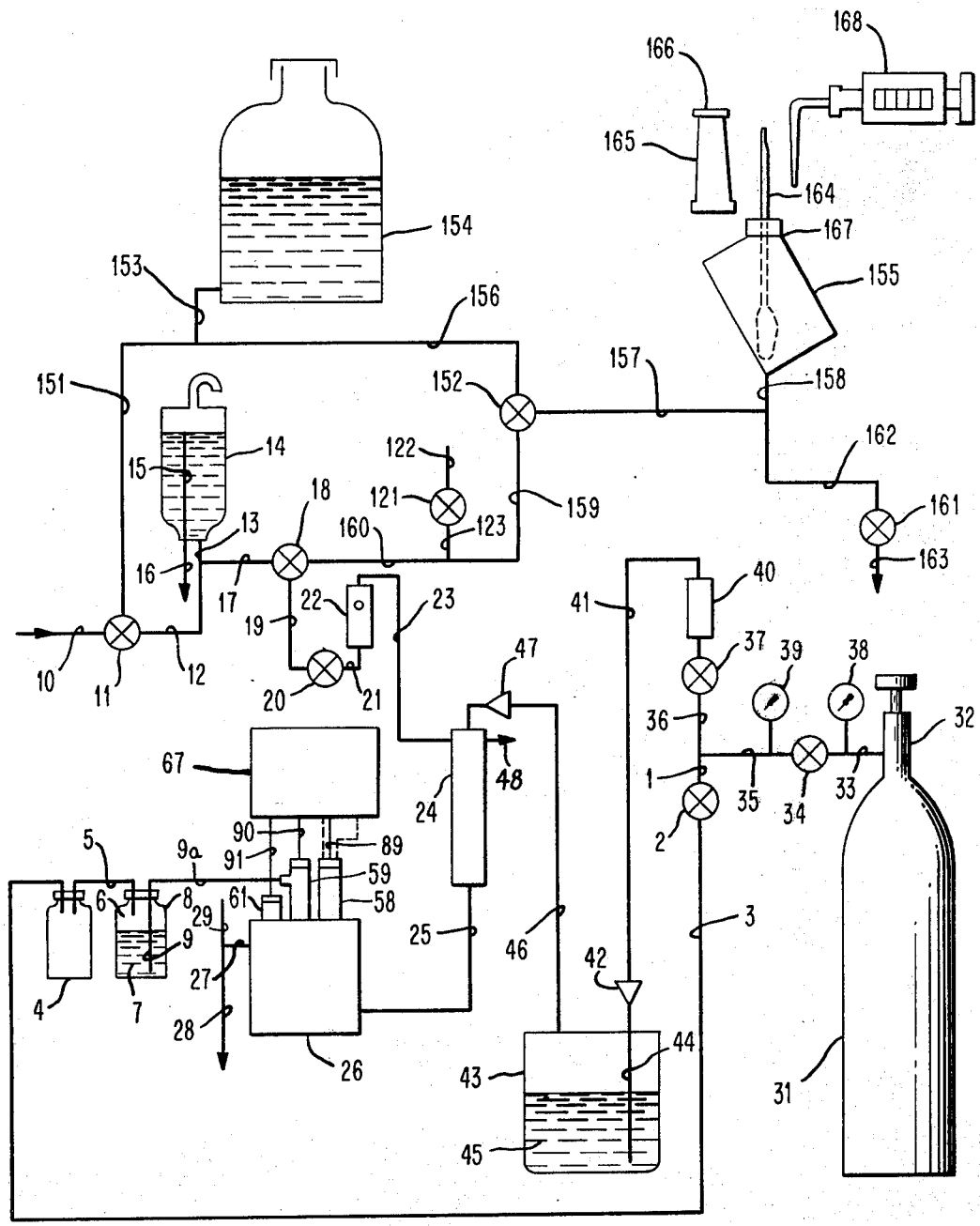
FIG. 1 is a flow sheet of a particular embodiment of the invention.

Studies indicate that relatively small cations, such as sodium, potassium, or ammonium, diffuse into the glass of the electrodes and associate themselves with specific sites available in the glass structure. In this way, they effect the electrode response. On the other hands, the larger cations are unable to relate themselves with the glass structure in this way.

It has been found that a group of bases having a molecular weight greater than 45 and having a dissociation constant greater in magnitude than $5 \times 10^{-5}$ produce in solution the larger cations which are unable by reason of their size to relate themselves to the glass structure of the electrode. Further, these strong bases are very effective in reducing the hydrogen ion content of the sample liquid. Examples of the group of bases which are suitable for use in accordance with this invention are listed in Table 1.

Table 1

Properties of Various Bases

| Compound | Dissociation Constant K Values at 25°C (× 10⁵) | Boiling Point °C | Vapor Pressure at 20°C mm Hg | Molecular Weight |
|---|---|---|---|---|
| Betaine | 1,450 (20°) | m.p.239 | | 117.15 |
| Sparteine | 570. | 325 | | 234.37 |
| Piperidine | 160. | 106.3 | | 85.15 |
| Pyroxilidine | 130. | | | |
| Diisopropyl Amine | 113. | 84.1 | 61.7 | 101.19 |
| Coniine | 100. | 168. | | 127.23 |
| Diethyl Amine | 96 | 56 | 195. | 73.14 |
| Phenylguanidine | 58.9 | | | |
| Triethyl Amine | 56.5 | 89.7 | 53.5 | 101.19 |
| Ethyl Amine | 56. | 16.6 | 873. | 45.09 |
| Isopropyl Amine | 53. | 32.4 | 455. | 59.11 |
| Dimethyl Amine | 52. | 7.4 | 1340. | 45.08 |
| Tetramethylene Diamine | 51 | | | |
| Diisobutyl Amine | 48 | 139–140 | | 129.25 |
| n-Amyl Amine | 43.9 | 99.1 | 31. | 87.17 |
| Isoamyl Amine | 43.9 | | | 87.17 |
| Methyl Amine | 43.8 | −6.3 | 1790. | 31.06 |
| n-Butyl Amine | 40.9 | 77.8 | 71.7 | 73.14 |
| α-Ethyl Pyrrolidene | 27. | | | |
| Methyldiethyl Amine | 27. | | | |
| Triisobutyl Amine | 26. | 191.5 | | 185.36 |
| n-Methyl Pyrrolidene | 15. | | | |
| Ethylene Diamine | 8.5 | 116.9 | 10.9 | 60.10 |
| Piperazine | 6.4 | 146.0 | 0.16 | 86.14 |
| Trimethyl Amine | 5.45 | | | 59. |

The properties of the foregoing bases may be contrasted with commonly used buffering agents, such as ammonia which has a dissociation constant of $1.77 \times 10^{-5}$ and a molecular weight of 17.03 and to morpholine which has a dissociation constant of $0.244 \times 10^{-5}$ and a molecular weight of 87.12.

It should be understood that bases that are suitable for use in accordance with this invention may, under normal conditions, be gases, liquids or solids.

Examples of ions that are produced from several of the bases of Table 1 are shown below: Ions produced respectively from the primary amines, methylamine, ethylamine and isopropylamine:

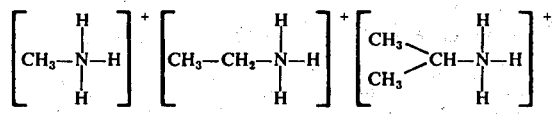

Ions produced respectively from the secondary amines, dimethylamine, diethylamine and diisopropylamine:

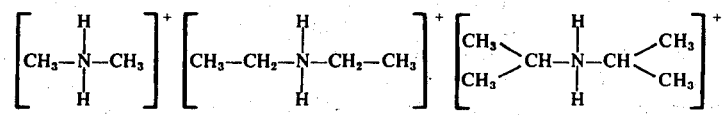

Ion produced from the tertiary amine triethylamine:

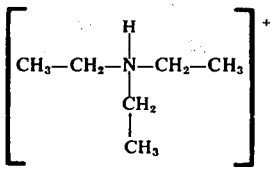

On the other hand, the ion produced from ammonia is:

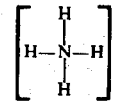

The above structural formulas dramatically show the effect of substitution on the size of the resulting positive ion. The ion of methylamine is appreciably larger than that from ammonia, but is quite a bit smaller than the ions from ethylamine and isopropylamine. The secondary amines offer more opportunity for substitution, as compared with the primary amines, with corresponding increase in ion size. It is interesting to note that the secondary amines diethyl and diisopropyl in addition to producing ions of large size are also quite strong bases, as reference to Table 1 will show. The dissociation constant of diethylamine is 54 times greater, and that of diisopropylamine, 73 times greater than that of ammonia.

Figure 2:
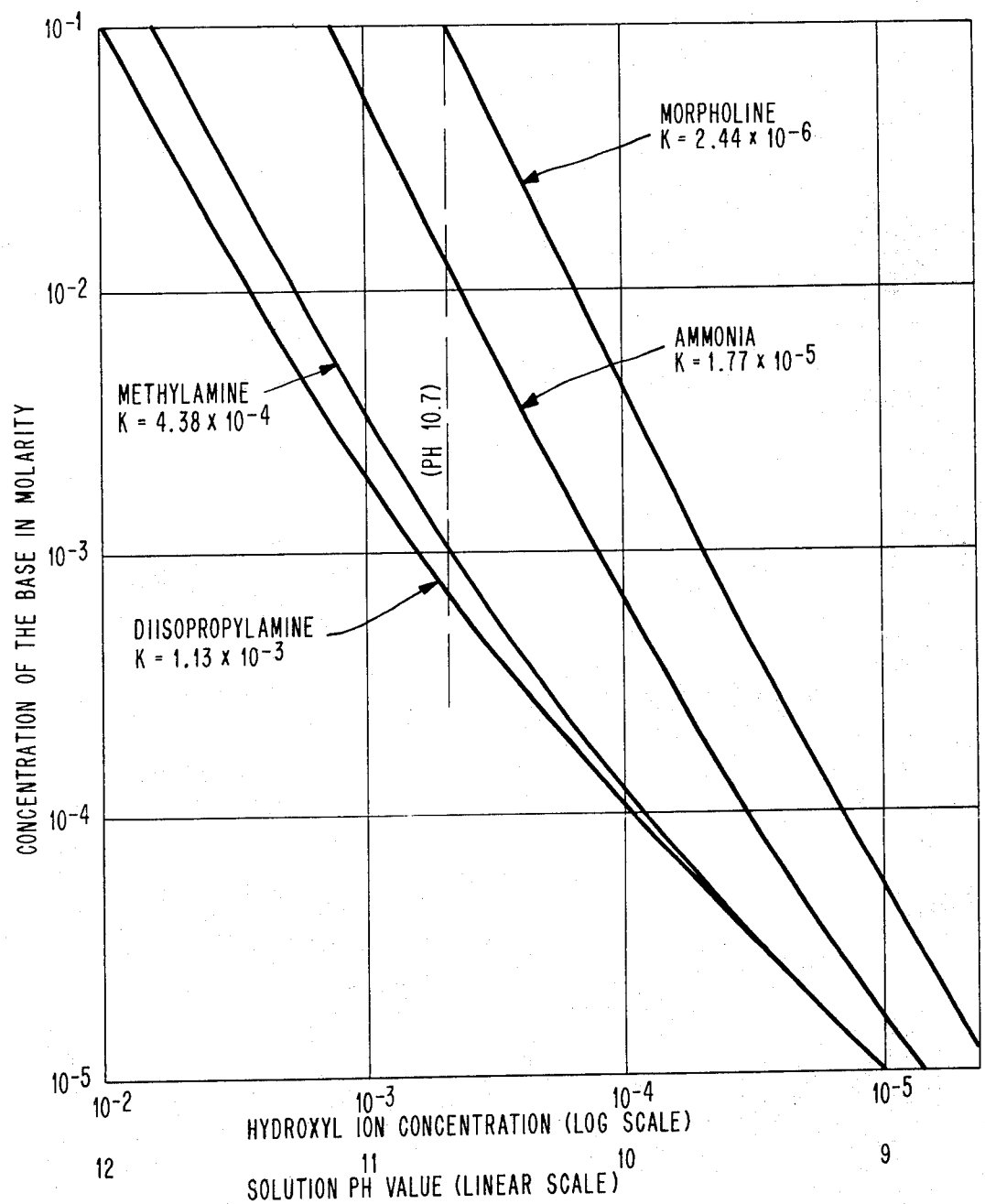
FIG. 2 shows plots of concentration of different bases as a function of hydroxide ion concentration.

The effect of dissociation constant on the hydroxide-producing capability of a base is graphically shown in FIG. 2. This figure shows the resulting pH value as a function of concentration, when each of four bases of different dissociation constant is added to pure water. Two of the bases, namely methyl amine and diisopropyl amine, are selected from the group of the present invention, while the other two, morpholine and ammonia, are prior art bases. The effect of dissociation constant is evident from the spread between the curves. At a concentration value of $10^{-3}$ molar, for example, morpholine, with dissociation constant of $2.44 \times 10^{-6}$ will produce a solution pH of 9.7; ammonia with a constant of $1.77 \times 10^{-5}$, a pH of 10.1; methyl amine with a constant of $4.38 \times 10^{-4}$, a pH of 10.7; and diisopropyl amine with a constant of $1.13 \times 10^{-3}$, a pH of 10.8. Moreover, the differences are greater at higher pH. Accordingly, bases with a larger value of dissociation constant are more efficient in producing the desired high pH property of the solution. For this reason, it is advantageous to chose a base having a dissociation constant at least as large as $5 \times 10^{-5}$. It is not difficult to find such a base, as all of the bases of Table 1 have dissociation constants exceeding this value. Moreover, the table is by no means complete with respect to available bases having dissociation constant greater than $5 \times 10^{-5}$.

Another way of expressing the effect of dissociation constant is to indicate the solution concentration values of the respective base substances that will be needed to produce the same pH of solution. Referring to FIG. 2, if a resulting solution pH of 10.7 be assumed, morpholine will have to be present at a concentration of about 0.1 molar; ammonia, 0.013 molar; methylamine 0.001 molar; and diisopropylamine, 0.0008 molar. Amounts of these substances needed on a weight basis will depend on the molecular weight figures, and for the preceding comparison, assuming one liter of solution in each case, the amounts will be 8.71, 0.17, 0.031, and 0.081 grams respectively.

Because quite different amounts of the various bases are needed, the cost of running equipment will obviously differ. In making a cost comparison not only will the mass rate of consumption of the base substance be important, but also the molecular weight and the price of the substance in commercial quantities as would be purchased for routine maintenance of the equipment. Cost comparisons made in this manner have indicated that both morpholine and ammonia are relatively expensive to use, with morpholine being appreciably more expensive than ammonia. The comparison was made assuming that the same final solution pH would be maintained in every case. The amount of morpholine needed to produce a satisfactory pH value (above pH 10.5) is too great for this agent to be considered practical.

Factors other than those discussed above must be considered. Particularly, safety, convenience of handling, long-term reliability and low maintenance requirements are important. A sodium ion concentration measuring system which meets the foregoing considerations is shown in FIG. 1. The system in FIG. 1 is for use with diisopropyl amine, but it will be appreciated that the system is suitable for use with other volatile liquid bases. Some of these bases are noxious and may present a fire hazard. However, liquid amines, and particularly liquid diisopropyl amine, are somewhat safer for use.

Also, the appreciable vapor pressure of these liquid amines offers an advantageous way of adding the amine to the sample water. The flow of a non-reactive gas through the amine can be used as an effective transport means. This technique permits the addition to be safely and conveniently made, at exactly controlled flow rate, and in a reliable manner over long periods of time. Since the amine in transferral passes through the vapor state, the method has the further advantage of protecting against sodium ion contamination, a real possiblity where liquid or solid amine is added directly to the sample solution. Other liquid bases with sufficient vapor pressure, besides diethyl and diisopropylamine, are available for use in the vapor transport scheme, and examples may be found in Table 1 and elsewhere. It should be understood that the method and apparatus now to be described comprise an important part of the present invention.

A schematic representation of equipment that uses the vapor transport scheme is shown in FIG. 1. Sample water to be analyzed enters the pipe 10 and flows through valve 11, pipe 12, pipe 13 and into overflow chamber 14. Excess flow passes into pipe 15 and is discarded through discharge pipe 16. A portion of the sample water passes through pipe 17, valve 18, pipe 19, flow regulating valve 20, pipe 21, flowmeter 22, pipe 23 and into the absorber 24. From absorber 24 the sample water passes through pipe 25, into the flow cell 26 where the electrode measurement of sodium ion is made, and then discharges through pipe 27 and is discarded through pipe 28. The overflow chamber 14 is located at an elevation above the absorber 24, which in turn is located in elevation above the flow cell 26. Hence the sample water is able to flow by gravity in the manner described. The open-ended stand pipe 29 ensures that the water in pipe 27 will discharge at atmospheric pressure, uneffected by the liquid flow in pipe 28.

A flow of non-reactive gas, such as nitrogen or air, is provided for amine transport. As shown in FIG. 1, nitrogen gas contained in the cylinder 31 passes through the cylinder shut off valve 32, pipe 33, pressure reducing valve 34, pipe 35, pipe 36, and through the flow control valve 37. Gauge 38 indicates cylinder pressure. The pressure reducing valve 34 operates to maintain essentially constant gas pressure in pipe 35, and this pressure is indicated by the gauge 39. The flow of gas as regulated by the valve 37 flows through the flowmeter 40, the pipe 41, the check valve 42 and then into the base containing vessel 43 through the pipe 44. The end of pipe 44 is located below the liquid level of the base 45. The gas flow thus bubbles through the supply base 45 and acquires a vapor concentration of base in amount approaching the equilibrium vapor pressure of the liquid at the existing temperature. The combined flow of gas and vapor discharges from vessel 43 through pipe 46, check valve 47 and into the absorber 24. Absorber 24 provides contact between the stream of sample water flowing through it and the gas and vapor stream entering through check valve 47. Since the water has a strong affinity for the vapors of the base, the base is substantially entirely absorbed by the sample water stream, leaving the nitrogen gas to discharge through pipe 48. The overall effect is to raise the pH of the sample water entering the measurement flow cell 26 to a value within the approximate range of 10.5 to 11.5.

The check valves 42 and 47 prevent mishap when the equipment is shut down. Check valve 42 prevents the flow of amine backward through line 41, while check valve 47 prevents flow of water into line 46.

The adjustment of flow rate is not critical, neither with respect to the sample water stream nor with respect to the gas stream. It has been found that a sample water flow rate of 125 ml./min. and a gas flow rate of 0.2 cu. ft./hr. are quite satisfactory, although these rates may be varied by a factor of 2:1 or more in either direction without harming operation. These values pertain to the use of diisopropylamine at a temperature of about 25°C when contained in a 5-gallon steel can (vessel 43). The amine vaporization rate is relatively small in magnitude, and only a moderate influx of heat through the walls of vessel 43 will be required to supply the needed latent heat of vaporization. If ambient temperature is considerably lower than 25°C, one might use an amine of greater vapor pressure; or at appreciably higher ambient temperature, an amine with lower vapor pressure than diisopropylamine. Latitude in adjustment of the relative flow rates is afforded by the fact that the measurement of sodium ion is not critically dependent upon maintaining an exact value of pH, so long as the pH value is in a range sufficiently high to repress hydrogen ion response of the electrode.

Polyethylene and stainless steel are satisfactory materials of construction and are recommended for use in the piping lines, the valves and fittings and other components of the system. Glass bottles and tubing and other glass items are to be avoided, as this material will introduce sodium ion contamination into the sample water. Also to be avoided are pipe dopes, greases, cements, and other materials commonly used to seal joints against leaks. The pipe threads may be sealed with the special Teflon material "Ribbon Dope Thread Sealant," supplied by Permacel, New Brunswick, New Jersey.

It should be pointed out that specific embodiments of some of the details of FIG. 1 need not be carried out exactly as shown. For example, the overflow chamber serves to provide a pressure of sample water to supply the flow control scheme indicated. Other methods of gaining flow control of the sample water would be quite satisfactory. Also the gas supply need not be from a cylinder. An air pump might be used or air might be drawn from an air service line, with proper precautions in every case to avoid dirt or other forms of contamination.

Although other sodium ion electrodes may be used, electrodes produced from L&N No. 914 glass are preferred (produced by Leeds & Northrup Company, Philadelphia, Pennsylvania). The cation-responsive membrane of this electrode is within the scope of published prior art.

The sodium ion electrode 58, the reference electrode 59, and the temperature compensator 61 are connected to conventional high impedance voltage measuring instrumentation 67 by means of the conductors 89, 90 and 91. The voltage measuring instrumentation 67 may take the form of an L&N 7405 pH meter provided with an L&N Speedomax Type H recorder for readout indication and recording. It is convenient to make the recorder display a 3-decade change in sodium ion concentration and to use 3-decade logarithmic chart paper (L&N 660,790). The recorder scale is made to match the above paper. In order to make the signal from the pH meter of correct magnitude, a dropping resistor of 46.67 ± 0.05 ohms is used across the output of the pH meter. With the automatic temperature compensator connected in the usual manner to the pH meter, the output reading of the recorder is automatically compensated for temperature change. Sodium ion electrodes usually exhibit response characteristics corresponding to the slope constant of the theoretical Nernst equation, that is, 59.16 mv. per decade change in concentration at 25° C. Sometimes, electrodes may give slightly less than theoretical response, but the response for a one decade concentration change will almost never be deficient by more than about 2 or 3 mv. which would introduce a negligible error in many applications.

At times, it may be desirable to calibrate the equipment for the specific characteristics. In this event, the automatic temperature compensator may be made adjustable to take care of this small error. Another way is to disconnect the automatic compensator 61 and to use the temperature dial of the pH meter to introduce the correct slope characteristic for the electrode. Details of how this is done and other calibration information is subsequently given.

LIQUID JUNCTION REQUIREMENTS

As compared with the usual industrial pH measurement, the measurement of sodium ion requires superior performance of the electrochemical cell. The reason is that ion measurement uses a full-scale voltage span that is appreciable less in magnitude than that in a 0–14 pH measurement (180 mv. versus 840 mv.). The output of the electrochemical cell in effect is being amplified and hence any noise (undesired signal variations) is also amplified.

It has been found that the liquid junction of the electrochemical cell can be a serious source of noise if the junction is not properly designed and operated. The high pH of the sample water as it flows through the cell appears to aggravate the liquid junction problem. In addition to the effect of high pH, there appears also to be susceptibility to flow rate changes or concomitant changes in hydrostatic head. A bad junction is indicated by a chart trace that exhibits hunting in a sporadic way. Sideways excursions of the record may amount to 5 or more millivolts. A bad junction may also cause a sudden sharp jump in the indicated potential occasionally amounting to 20 or 30 mv. in magnitude, depending on particular cell and junction conditions. Noise of this kind is intolerable and has been observed to a serious extent in prior art systems.

In accordance with an important aspect of this invention, many of the difficulties previously associated with liquid junction operation are obviated by operating the junction under considerably greater hydrostatic pressure difference than usually employed. Pressures on the order of 4 to 8 psi should be used and may even be greater than this if the potassium chloride leakage rate does not become excessive. Under pressurized conditions, a small porous plug may be advantageously used in the present invention to provide the reference solution leakage path. Junction devices of this type are commercially obtainable (A. H. Thomas Company, Cat. No. 4857-F15) but must be modified to accommodate the pressure line.

Although the pressure may be applied in other ways, the pressurizing means shown in FIG. 1 is particularly advantageous. Gas pressure is used to drive the potassium chloride solution into the reference electrode. Nitrogen gas pressure of 4 to 8 lbs. per square inch contained in pipe 35 is led through pipe 1, valve 2, pipe 3, trap 4, pipe 5, and into the gas space 6, over the supply of potassium chloride solution 7 contained in reservoir 8. The gas pressure exerted in space 6 forces potassium chloride solution to flow into the immersed tube 9 and thence through the connecting pipe 9a and into the reference electrode 59. The 4 to 8 lbs. of pressure as indicated by the gauge 39, which is connected to the pipe 35, will cause the equivalent of about 110 inches to 220 inches head of potassium chloride solution. The function of the trap 4 is to prevent accidental back flow of potassium chloride solution in the line 3 if the gas pressure is suddenly reduced. For corresponding reasons and also to ensure proper functioning of the reference electrode 59, the equipment should be assembled with no air, or a minimal amount of air, trapped in the lines 9 and 9a and inside the reference electrode 59.

THE ABSORBER, FIG. 3

Figure 3:
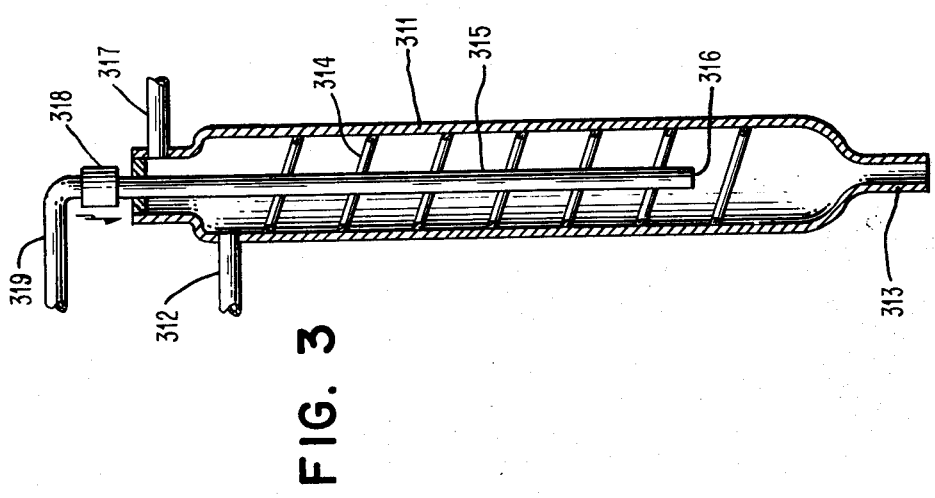
FIG. 3 shows the absorber.

The absorber shown in FIG. 3 is advantageous in allowing optional use of either a gaseous amine (such as dimethyl amine) or a transported vapor formed from a liquid amine (diisopropyl amine) without requiring equipment change. (In this specification, the term "gaseous base" includes a vapor base, as well as a base which is naturally in gaseous form.) This absorber also has the advantage, if the normal amine flow should stop for any reason, of avoiding suck-back of the sample liquid back into the base supply.

An elongated cylindrical chamber 311, mounted vertically, is provided in its upper region with a sample solution inlet pipe 312 and in its lower region with a sample solution outlet pipe 313. The interior of chamber 311 may be provided with a baffle 314 in the form of a helix which fits against the interior wall of chamber 311 and which serves to spread the flow of sample solution uniformly over the interior surface of chamber 311. The chamber is also provided with an amine supply tube 315, the discharge end 316 of which is located in the middle of the space in a region near to but not at the bottom of chamber 311. The top of chamber 311 is provided with a vent pipe 317 the check valve 318 is interposed in the pipe line 319 that leads to the amine supply tube 315. Dimensions of the parts are chosen such that when sample solution flows through chamber 311 it never comes in contact with the discharge end 316 of amine pipe 315.

The flow of amine, either as a gas coming directly from a cylinder or as a vapor carried by inert gas from a liquid reservoir enters pipe 319, flows through check valve 318, tube 315 and discharges inside chamber 311. Inside chamber 311, the amine gas or vapor flow is upward but very rapidly becomes absorbed in the sample water that is flowing downward along the interior wall of chamber 311. If non-reactive carrier gas is used, this gas will traverse the length of chamber 311 and discharge from pipe 317.

Since the discharge end 316 of the amine line is normally never in contact with liquid water, water can not suck-back through the amine line if flow of amine stops. In the case of flooding caused by improper, excess sample water flow, the check valve will protect the amine line. Also, the amine tube 315 may be made of narrow bore so that the velocity of amine flow will be greater than the counter flow velocity of water absorption.

The vent 317 which communicates the interior of the chamber with the atmosphere is quite important whether a transported vapor or a pure gaseous base is introduced into the absorber, as it is essential to maintain the interior of the chamber at atmospheric pressure. When the transported vapor technique such as that shown in FIG. 1 is used, the vent 48 allows the escape of the inert gas to the atmosphere, thereby preventing pressure build-up. When pure gaseous base is introduced, the vent avoids a reduction in pressure below atmospheric that might occur as gaseous base dissolves in the liquid sample. Negative pressure is undesirable as it might lead to suck-back already mentioned, and furthermore, if sample flow stops might cause withdrawal of sample liquid from the measurement cell, thereby leaving the ion sensing membrane of the electrode undesirably exposed.

ANALYZER CELL CONFIGURATION, FIG. 4

Flow cells of conventional type are objectionable primarily because they do not adequately take care of the potassium chloride leakage that comes from the reference electrode. As has already been indicated, a sodium ion electrode will respond to potassium ion if the concentration level is of a magnitude to satisfy the requirements of the selectivity ratio constant. As previously discussed, it is desirable to operate the reference electrode with a relatively full flow of potassium chloride solution passing through the junction and into the sample water stream. Accordingly, appreciable amounts of potassium ion are introduced in the sample stream. Potassium choride solution introduced into the sample stream has an appreciably higher density than the sample water, and hence tends to stratify in the region at the bottom of the sample stream. In a flow cell of conventional construction, the motion of the stratified potassium chloride layer is not necessarily in the same direction as the nominal direction of water flow through the cell. The potassium chloride solution may undergo a circulatory movement within the cell, with some of the more dense stratified layer moving in a direction opposite to the nominal flow direction through the cell. Hence, even though the reference electrode is mounted downstream from the glass electrode, ctrode, the potassium chloride solution at times is able to work its way upstream against the flow and come into contact with the glass electrode to produce a false reading.

Figure 4:
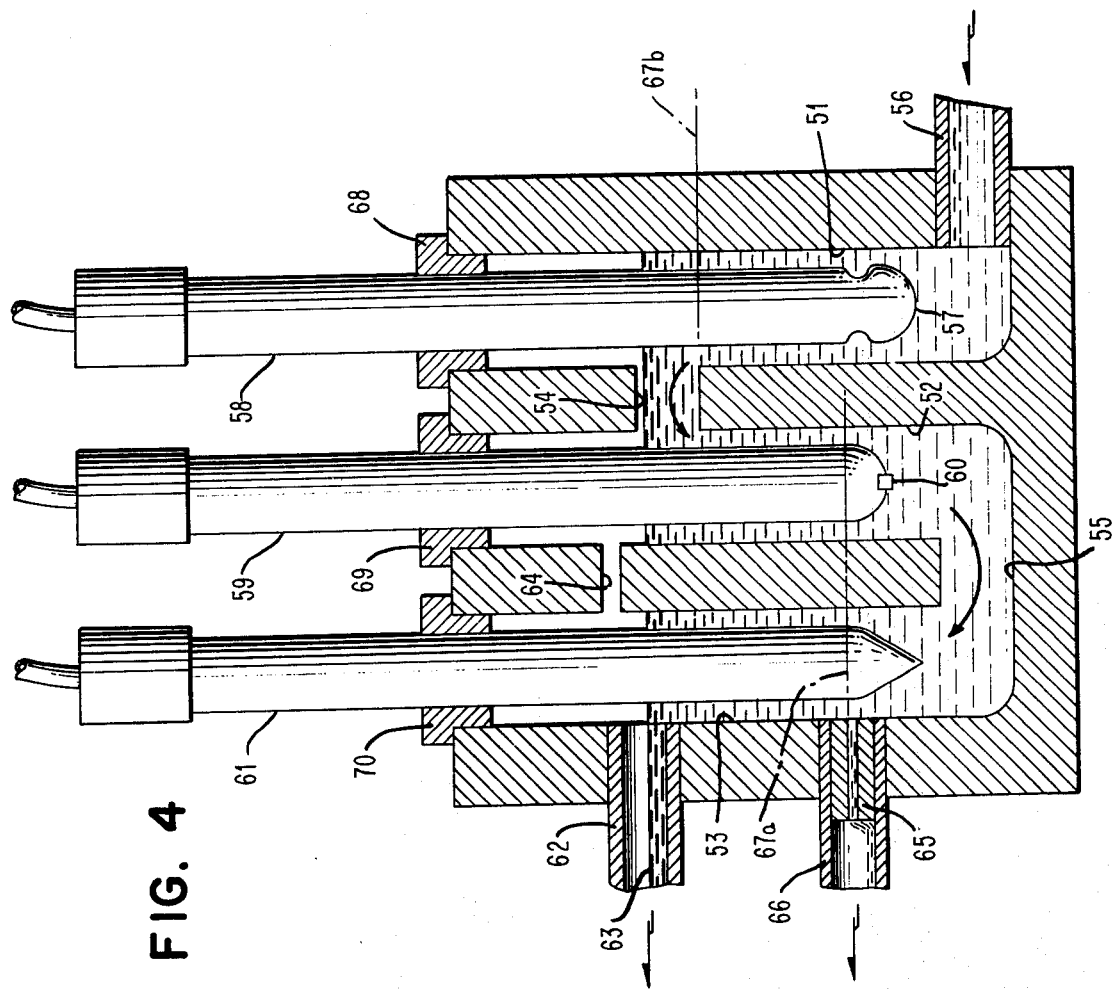
FIG. 4 shows the analyzer cell.

To overcome this undesirable effect, the cell configuration of FIG. 4 is provided. Three vertically oriented chambers 51, 52 and 53 are bored in a block of polyethylene. Flow communication between chambers 51 and 52 is provided by passageway 54. Communication between chambers 52 and 53 is provided by the exit port 55.

In normal operation, sample water enters by way of the pipe 56 located at the bottom of chamber 51. The water flows upwardly, promptly makes contact with the ion sensitive membrane 57 of the glass electrode 58, and thence continues its upward flow through the annular space between electrode 58 and the wall of the chamber 51. Solution flow then passes to chamber 52 by means of the fluid passageway 54, and proceeds downwardly in the annular space between the reference electrode 59 and the wall of chamber 52. Before leaving chamber 52, the solution makes contact with the liquid junction interface 60 of reference electrode 59 and then passes into chamber 53 via exit port 55. Solution flow then proceeds upward through the annular space between automatic temperature compensating unit 61 and the wall of chamber 53 and finally exits through the discharge pipe 62. It will be noted that the downward flow of solution through the relatively narrow annular space around reference electrode 59 effectively prevents the potassium chloride solution leaking from liquid junction interface 60 from finding its way into chamber 51 and making contact with the ion sensitive membrane 57. The more dense potassium chloride solution will always tend to flow downward with the current, rather than upward. Although there may be some small accumulation of potassium chloride solution in the exit port 55, the flow of water towards the discharge pipe 62 will eventually carry the potassium chloride out of the cell.

The height of discharge pipe 62 will determine the normal water level 63 in the cell. The height of fluid passageway 54 is positioned so that this passageway will be substantially filled with solution when solution flows in the normal manner through the cell. Thus the electrolytic conduction path between the ion sensitive membrane 57 and the liquid junction interface 60 will be properly maintained. The passageway 64 located a little above the normal solution level 63 ensures that the upper part of chamber 52 does not become airbound.

Trouble from potassium chloride reaching the glass electrode may occur during down time when there is no sample flow through the cell, unless provisions are made to take care of the situation. If the cell stands filled with quiescent solution, potassium chloride can diffuse from the reference electrode chamber 52, through the passageway 54 and into the glass electrode chamber 51, where it will eventually come into detrimental contact with the ion sensitive membrane 57. To prevent this from happening, the cell may be provided with a leakage path that allows some cell solution to discharge through the flow regulating tube 65 and into the drain pipe 66. The leakage rate as determined by the bore of the tube 65 is made substantially less than the normal sample flow rate through the cell. Hence in normal operation the water level in the cell will be maintained at the level 63 as previously described. When the flow of water to the cell stops, however, the leakage path will let the water level in chambers 52 and 53 fall to the level 67a, and that in chamber 51, to the level 67b. When this happens there will no longer be solution continuity between chambers 51 and 52 and therefore no possibility of back diffusion of potassium chloride electrolyte to interfere with the sodium ion electrode. The electrodes may remain for protracted periods of time in contact with the solutions that remain in their respective chambers. When sample water flow commences again, the electrodes will be in satisfactory condition to begin measuring the sodium ion concentration. With some forms of liquid junction it may be desirable to position tube 65 and pipe 66 to make the liquid level 67a fall below the junction interface 60, thereby causing the junction interface 60 to be non-immersed during standby periods.

It should be noted that the electrolytic conductivity of the amine treated sample water is relatively high, as compared with the very low conductivity of untreated sample water as it may come to the analyzer. Hence, the flow cell should not exhibit interference caused by streaming potential effects. It should further be pointed out that Hysol or epoxy construction of the flow block may cause serious electrode interference problems in the presence of amine, and accordingly such material should be avoided. Polyethylene may be used and the mounting collars 68, 69, and 70 may also be made of polyethylene. The conventional materials of construction used for these parts (synthetic rubber and the like) should be avoided.

THE AMINE RESERVOIR, FIG. 5

Figure 5:
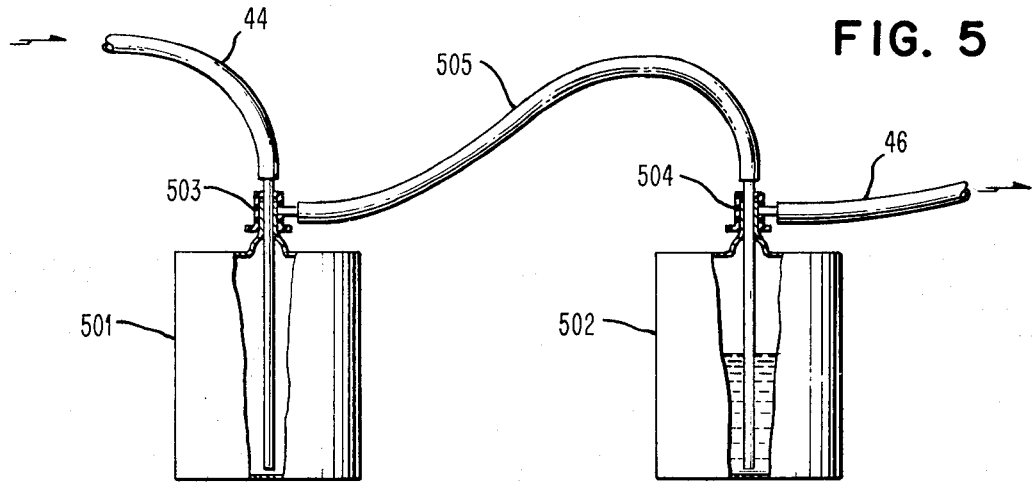
FIG. 5 shows an advantageous arrangement for the amine reservoirs.

In FIG. 5 there is shown an advantageous arrangement of the amine reservoirs. Since amine is somewhat noxious and volatile, disposal of amine which remains in the bottom of the reservoir when the supply in a can becomes low is a problem. The arrangement in FIG. 5 disposes of all amine from a can before the can is discarded without requiring the operator to transfer amine. The arrangement also insures against inadvertently running out of amine with resultant equipment shutdown. Maintenance requirements are reduced.

The arrangement includes two amine reservoirs which are cans 501 and 502. Each can is fitted with a vaporizing tube assembly 503 and 504. These include a tube which extends to the bottom of the can. The jumper tube 505 connects the two cans. The tube 44 from the inert gas supply is connected to the assembly 503. The tube which leads to the absorber is connected to the other assembly 504. When the can 501 is empty, can 502 is moved to its position. A fresh can is placed in the previous position of can 502.

As a modification of the reservoir system described above, it will be advantageous to provide caps which can be removed from the cans without disconnecting the tubing 44,, 505 and 46 from the vaporizing tube assemblies. In this case, each vaporizing tube assembly is provided with a screw cap which fits the conventional amine can. The screw cap is rotatable on the tube so that the cap can be unscrewed without turning the assembly. This allows the entire assembly to be removed from the can 501 and replaced onto the can 502 when it is desired to change cans. Above the screw cap a lock nut, also rotatable on the tube, is provided to secure the cap and to seal the interior of the can.

ALTERNATIVE INSTRUMENTATION SYSTEMS

Although the instrumentation scheme illustrated in FIG. 1 operates very satisfactorily and may be considered a preferred arrangement,, it should be understood that alternative ways of arranging the equipment may be used. Substances suitable for adding to the sample water to produce the desired measurement conditions may at ambient temperatures be gases, or liquids of low or high vapor pressures, or solids. Hence, the vapor transport scheme of FIG. 1 will not be applicable in all cases.

GASEOUS AGENTS

It will be noted in Table 1 that dimethylamine with dissociation constant of $52 \times 10^{-5}$ will be quite satisfactory as an agent for making the sample water basic. Also, its molecular weight of 45.08 and the two methyl radicals on the nitrogen atom will effectively prevent the positive ion of this amine from adversely affecting the sodium ion electrode. Dimethylamine will thus be satisfactory as an addition agent, but its boiling point at 7.4° C and its vapor pressure of 1340 mm of mercury at 20° C indicates the gaseous state under ordinary conditions.

Figure 6:
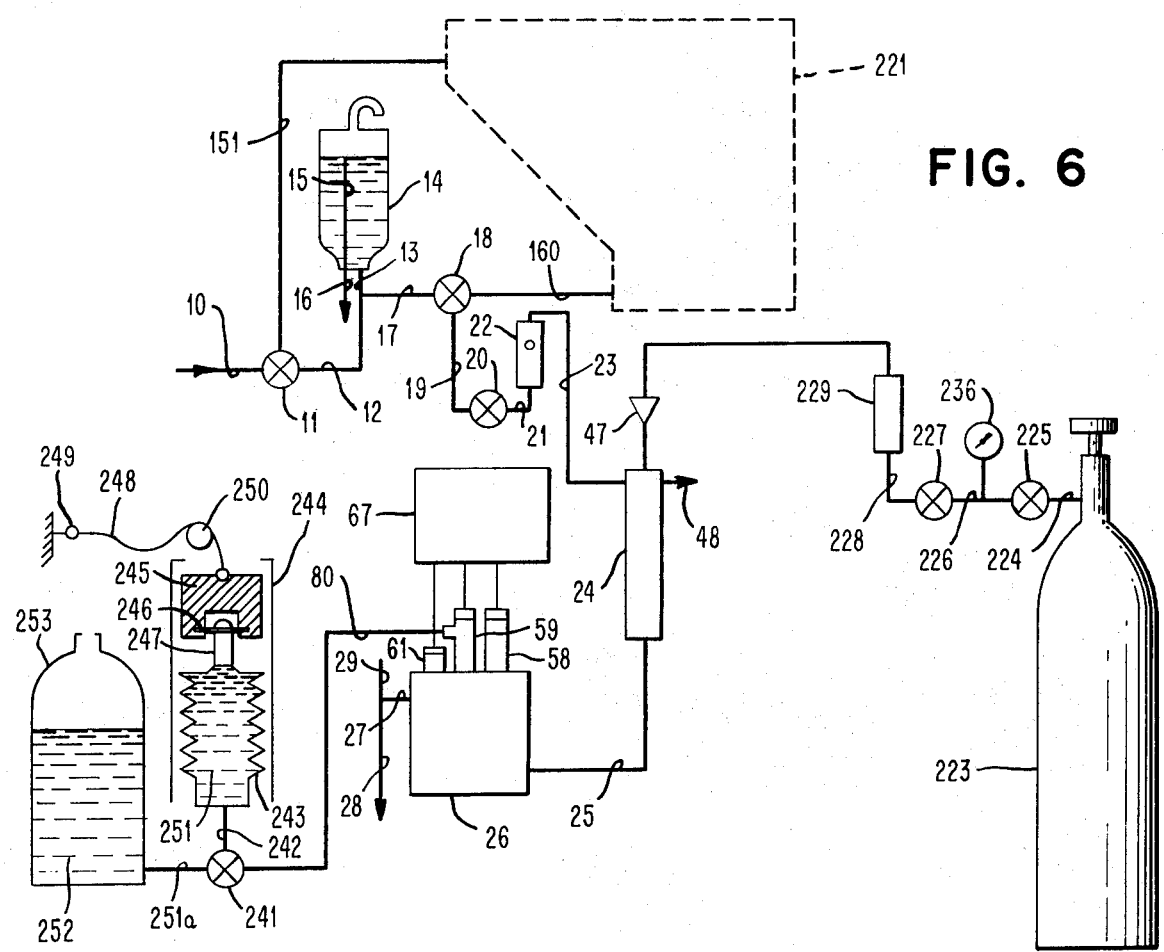
FIG. 6 shows a flow sheet of an alternate embodiment of the invention.

Dimethylamine can be used as the addition agent in a system as illustsrated in FIG. 6. Parts of the equipment that are labeled with the same numbers as in FIG. 1 have the same functions as corresponding parts in FIG. 1. The parts used for the calibration procedure have been omitted in FIG. 6 and are indicated by the dotted block 221. The modified part of the diagram relating to the introduction of gaseous amine will now be described.

Sample water flowing through pipe 23 enters the absorber 24 and proceeds through pipe 25 to the measurement cell 26. The gaseous amine is contained under pressure in the cylinder 223. Amine in gaseous form flows through pipe 224, pressure reducing valve 225, pipe 226, flow control valve 227, pipe 228, flowmeter 229, and check valve 47 into absorber 24. The check valve 47 is an added precaution to prevent accidental backflow of sample water.

The amine gas pressure in pipe 226 is controlled by adjusting the pressure reducing valve 225 and is measured by means of the gauge 236. The rate of amine gas addition to the absorber 24 is controlled by adjusting the valve 227 and is measured by the flowmeter 229.

It will be observed in the system of FIG. 6 that a supply of non-reactive gas (nitrogen) under pressure is not available to operate the reference electrode 59 in the desired pressurized manner. Accordingly, an alternative method of pressurizing the reference electrode is illustrated in FIG. 6. The electrolyte chamber in reference electrode 59 communicates by means of pipe 80 with 3-way valve 241, pipe 242 and with the bellows chamber 243, which may be of polyethylene construction. The bellows is surrounded by a loose fitting tubular guide 244. A weight 245 fits loosely in the upper portion of the guide 244 and is connected by the pin 246 to the bellows handle 247. A cord 248 attached to the fixed point 249 passes over the pulley 250 and connects with the weight 245. The volume within bellows 243 is a variable depending on conditions and is kept filled with potassium chloride solution 251. In normal operation when valve 241 is set to communicate between pipes 242 and 80, the downward force of the weight 245 exerted on the bellows handle 247 creates a positive solution pressure of 4 to 8 psi inside bellows 243 which is transmitted through pipes 242 and 80 to the reference electrode 59. When the volume inside the bellows 243 diminishes to the point where replenishment of solution is necessary, valve 241 is turned so that pipe 242 communicates with the pipe 251a and the reserve supply of solution 252 contained in the reservoir bottle 253. Simultaneously the cord 248 is pulled with the hand so as to counteract the gravitational force of weight 245 and to raise the position of the bellows handle 247, thereby allowing the bellows chamber 243 to expand and draw in solution from reservoir 253. When the bellows chamber 243 is expanded to its maximum size, valve 241 is returned to the first position establishing solution communication with pipes 242 and 80 and with electrode 59. When hand tension on cord 248 is relaxed, pressurized flow of electrolyte to the electrode returns to normal condition.

It should be understood that a piston and cylinder, such as a large volume syringe, may take the place of the bellows 243. The weight 245 or a spring may be attached to the handle of the syringe piston to exert a suitable driving force. The syringe cylinder will provide mechanical guidance for the piston and force. With the guide tube 244 removed, the refilling operation can be performed directly by lifting the syringe piston and weight 245 to cause solution to flow into the displacement space inside the cylinder.

NONVOLATILE LIQUID AGENTS

Reference to Table 1 will show that some of the listed substances of satisfactory dissociation constant value have rather high boiling points, and hence would exhibit rather low vapor pressures at ordinary temperatures. In this category might be mentioned coniine and diisobutylamine. Another suitable material in this category (not included in Table 1) is the commercially available mixture of isomers of diamylamine, quoted as having a boiling point of 190° C and a vapor pressure of 0.3 mm of mercury at 20° C. These isomers are strong bases; the dissociation constant of diisoamylamine is $77 \times 10^{-5}$. The use of a gas-vapor transport scheme as in FIG. 1 for substances such as these would be difficult or impossible to carry out because of the very low vapor pressure.

Liquids of low vapor pressure can be added to the sample water by a scheme that allows a small, controlled flow of the liquid agent to enter the sample water stream directly. The sample water stream is under flow control as has already been described. If flow control is also applied to the liquid agent stream, the final concentration of amine in the sample water will be held constant, within satisfactory tolerance as determined by the precision of flow control of the two streams. It will suffice for the flow control of each stream to be approximate, as the concentration of agent in the sample water may be allowed to vary within limits to obtain satisfactory operating conditions.

The flow of the added agent may be controlled by any one of a number of techniques. A metering pump of conventional type may be used. The agent may be fed at constant head through a flow impeding device, such as a capillary tube or a porous frit. The flow of the liquid agent from a container may be controlled by slow displacement, affected for example by the controlled small flow of gas into the space above the liquid agent in the container.

Figure 7:
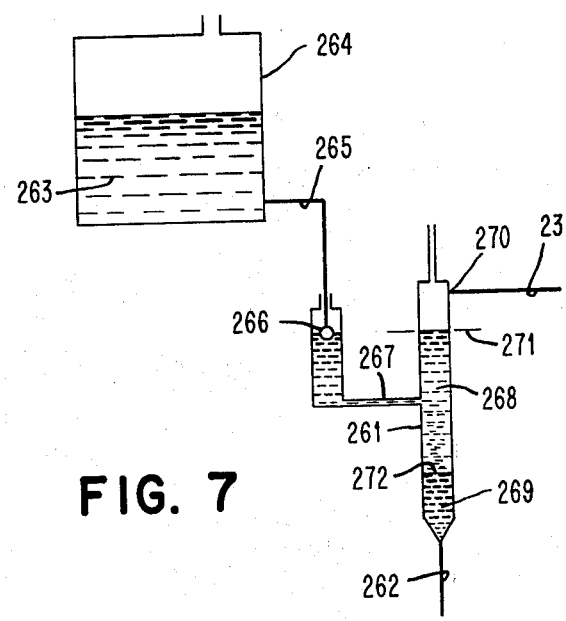
FIG. 7 shows an alternate absorber.

A method for controlling the flow of liquid agent into the water stream based on limited solubility of the agent in the water, is illustrated in FIG. 7. the solubility of dibutylamine in water is 0.47 percent by weight. The corresponding property for diamylamine is 0.07 percent. A saturated water solution of diamylamine (molecular weight 157.3) would be 0.0045 normal, a satisfactory value as reference to FIG. 2 will indicate.

In FIG. 7, sample water flows as previously described, reaching the pipe 23, which conducts the stream into the treating unit 261. After acquiring a concentration of treating agent approaching the solubility limit, the sample water flows through pipe 262 to the flow cell where measurement of sodium ion content is accomplished as previously described. Liquid treating agent 263 contained in a reservoir 264 flows through pipe 265, level controlling valve 266 and then through pipe 267 into the treating unit 261.

Most organic bases have a specific gravity less than that of water; the specific gravity of diamylamine is 0.77. Accordingly, an immiscible layer of this agent will float above the water phase in which it is in contact. Inside the treating unit 261 of FIG. 7, the organic agent phase 268 is shown above the aqueous phase 269. The water inlet port 270 is located at the top of the treating unit 261. Hence in flowing through the unit the aqueous phase must pass through the organic agent phase 268 before reaching the aqueous phase 269. In passing through the organic agent phase 268, the sample water stream absorbs some of the organic agent to an extent limited by the solubility relationship. The design of the treating unit 261 is such as to prevent emulsification or carryover of liquid agent into the aqueous phase flowing through pipe 262 into the measurement cell 26. (FIG. 1)

The amount of organic agent in the treating unit 261 is controlled by the liquid level controller 266 which maintains the level 271. The height of the pipe carrying effluent from the analyzer cell controls the discharge level and hence the pressure exerted in one arm of the liquid system. The pressure in the other arm is controlled by the level 271.

The height of the level 271 is a little above the height of the level in the analyzer cell because of the lower density of phase 268 as compared with phase 269. To maintain this differential level constant as will be necessary, the amount of organic agent 268 between the levels 271 and 272 must remain constant, thereby maintaining equal hydrostatic heads in the two sides of the liquid system. The automatic controller 266 may be of the chicken-feeder type or it may be a float controlled valve as shown.

With the system operating as described, the sample water in flowing to the analyzer cell will acquire the desired basic property by dissolving a controlled amount of the liquid base agent during its passage through the treating unit 261. Liquid base agent will be automatically supplied from the reservoir 264 as needed to maintain the desired quantity in the treating unit 261.

The equipment arrangement of FIG. 7 does not use pressurized gas, and hence some means other than that described in connection with FIG. 1 must be used to achieve the flow of potassium chloride solution into the reference electrode under suitable pressure. The method described in connection with FIG. 6 may be used for this purpose.

AGENT ADDITION BY DIFFUSION

Figure 8:
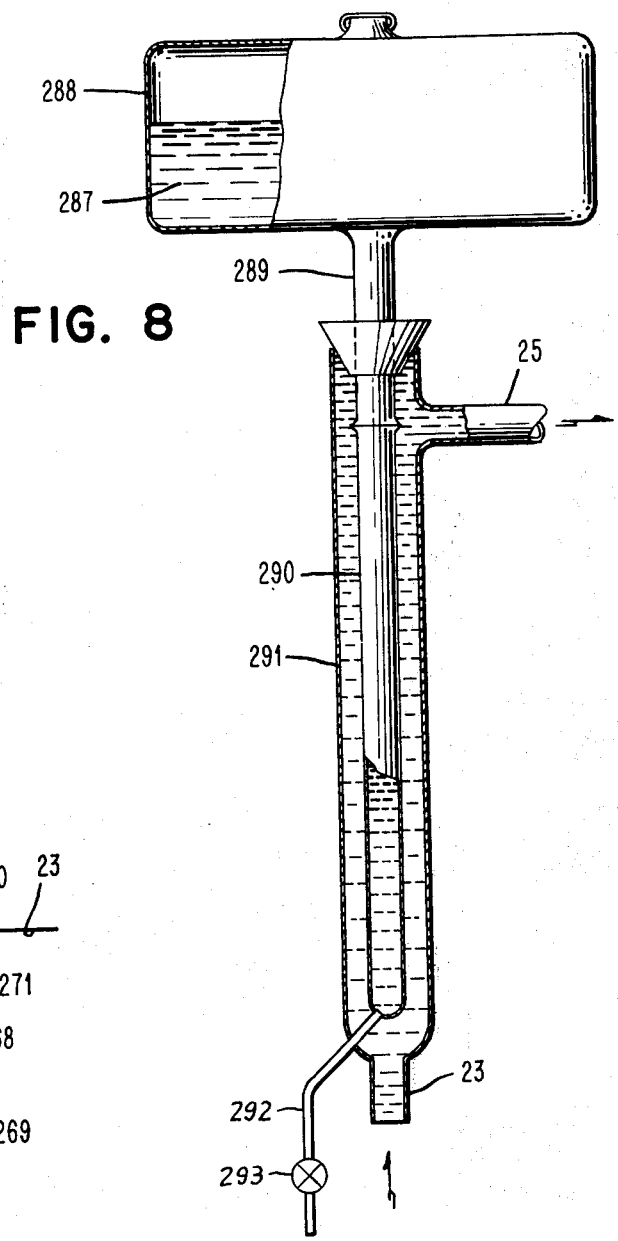
FIG. 8 shows another type of absorber.

Liquid and gaseous agents may be introduced in controlled manner by letting them diffuse through a suitable diaphragm material and into the sample water stream. One form of equipment for diffusion transfer of liquid agent is illustrated in FIG. 8. The base agent 287 contained in reservoir 288 flows through pipe 289 and into the diffusion tube 290, which is substantially closed at the far end. Sample water entering through pipe 23 flows into jacket 291, passes upwardly through the annular space surrounding diffusion tube 290, exits through pipe 25 and proceeds to the flow cell for sodium ion measurement. As agent diffuses through the wall of tube 290 it is absorbed in the sample water stream flowing along the outer wall of the tube.

While the tube 290 may be constructed so that diffusion is primarily from the base agent supply into the sample water, some sample water may diffuse back into the tube 290, thereby producing an aqueous solution inside the tube 290. In order to minimize this effect, the vent 292 in the bottom of the tube 291 provides for controlled discharge of base agent from tube 290. Valve 293 may normally be kept closed and periodically opened for a brief period to flush tube 290, or it may be adjusted to cause a slow leakage flow to allow continuous purging of tube 290.

The properties and dimensions of diffusion tube 290 are chosen to establish a proper rate of diffusion to produce the desired agent concentration in the sample water. The rate at which agent diffuses can be calculated from well known principles and will be proportional to the pertinent permeation constant, the area of the wall of the diffusion tube and the reciprocal of its thickness. The diffusion tube may be made of a plastic material such as polyethylene or silicone rubber. The equipment may take forms other than that illustrated in FIG. 8 to adapt to available forms of diffusion membrane materials and to the specific requirement imposed by the diffusion process.

CALIBRATION PROVISIONS AND PROCEDURES

Successful field operation of an analytical instrument will depend on the convenience and reliability of the particular means and techniques used for keeping the instrument in calibration. Hence, the calibrating techniques and equipment now to be described are considered an important part of the present invention. It should be understood that the use of these techniques is not necessarily limited to ion measurement systems, but may be applied to other instrumentation, particularly where a logarithmic scale response is obtained.

PROVISIONS FOR CALIBRATING

Referring to FIG. 1, the 3-way stop cock 11 permits the stream of sample water in pipe 10 to be diverted into pipe 151, from whence with stop cock 152 closed it flows into pipe 153 and reservoir bottle 154 (of about 5 gallons capacity). The supply of sample water in overflow chamber 14 is sufficient to keep water flowing through the analyzer system while reservoir bottle 154 is being filled. When reservoir 154 is filled, stop cock 11 is returned to the normal position thereby closing pipe 151 and causing water to flow in the usual manner through pipe 12 and into the overflow chamber.

Reservoir bottle 154 is located at an elevation above the mixing chamber 155, which in turn is located at an elevation a little above the normal water level in overflow chamber 14. Hence when 3-way valve 152 is turned to connect pipe 156 with 157, water from the reservoir bottle 154 will flow through pipes 153 and 156, valve 152, pipes 157 and 158 and into the mixing chamber 155. With valves 152 and 18 turned appropriately, water from the mixing chamber 155 will flow through pipes 158 and 157, valve 152, pipes 159 and 160 and through valve 18 into the sodium ion measurement part of the system. When valve 161 is open, water will discharge from the mixing chamber 155 through pipes 158, 162 and 163. When valve 152 communicates with pipes 156 and 157, and when valve 161 is open, the contents of reservoir 154 may be discharged through the pipes 153, 156, 157, 162 and 163. With appropriate positioning of valves 152 and 18, water from reservoir 154 may be run through pipes 153, 156, 159, 160, 19, 21, 23 and 25 and into flow cell 26 for measurement of sodium ion concentration.

The mixing chamber 155 is provided with a stirring paddle 164, which is customarily kept in the chamber 155 as shown. A spout 165 provided with a cap 166 fits over the projecting handle of the stirrer 164 and furnishes a protective cover for the neck of the chamber 155. The neck of the chamber 155 has a reference position 167 to mark the water level when the chamber is filled. Also, a 1 ml. micro-pipette 1688 is provided. The micro-pipette may be a "Digi-Pet" unit as supplied by Manostats Corporation, and should have its glass delivery tip bent at a right angle as indicated in FIG. 1. All other parts of the equipment that come in contact with sample water, should be constructed of polyethylene or stainless steel, as mentioned earlier.

CALIBRATING PROCEDURE

The calibrating procedures of this invention make use of the logarithmic relationship between the voltage on the electrodes and the concentration of the solution being measured. In the absence of interferences, the response of the electrode essentially follows the Nernst equation:

$$E = E_o + B \log c \qquad (1)$$

where
E is the voltage of the electrode,
c is the sodium ion concentration (activity), and
$E_o$ and B are constants at constant temperature.

When the electrode operates theoretically, the value of the constant B will be proportional to absolute temperature. At the low concentrations used in this work, the concentration values can be used interchangeably with the fundamentally more correct activity value. Full calibration of the instrument requires that appropriate instrument adjustment be made for the zero or bias constant $E_o$ and for the slope constant B.

Figure 9:
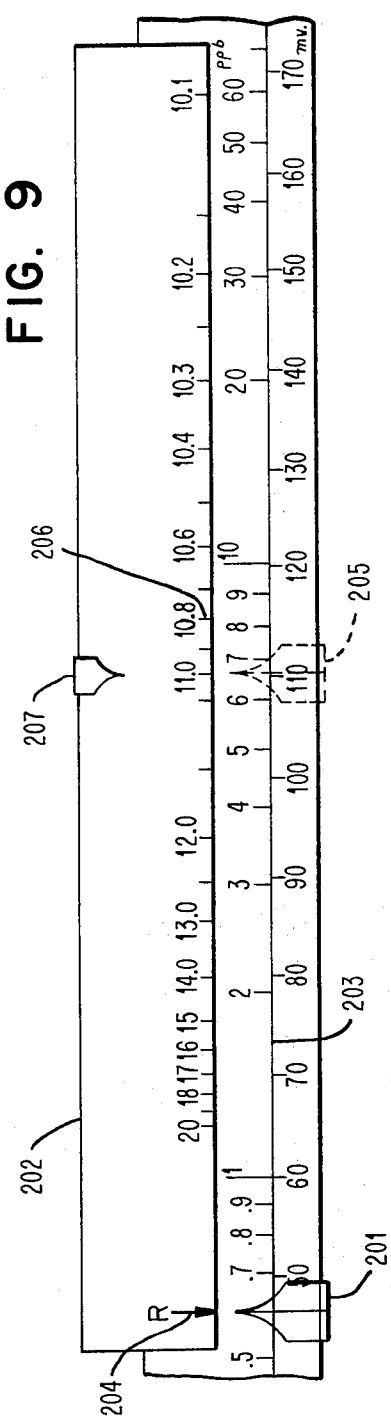
FIG. 9 shows the meter scale and an auxiliary scale.

The calibration procedure can be better understood with reference to FIG. 9 which shows the scale of the concentration measuring meter.

As for the first step in the procedure, a first sample from the sample fluid stream is introduced into the reservoir 154. (FIG. 1). This first sample has an unknown concentration since it is assumed that the system is not yet in calibration.

By proper adjustment of the valves as previously described, this sample fluid of unknown concentration is supplied to the analyzer cell 26. This will produce a reading on the meter as indicated by the position 201 of the indicator. As shown in FIG. 9 the meter is indicating a reading of approximately .6 parts per billion.

On FIG. 9 there is also shown a voltage scale below the concentration scale. The position 201 of the indicator is reading a voltage value of approximately 45 millivolts. This voltage reading will be denoted $E_a$.

The next step in the calibration procedure is to mix a sample having a known concentration increment above the unknown concentration.

As previously described, this second sample is mixed in the mixing chamber 155. By using the pipette 168, a known amount of ionic material is added to a known volume of sample fluid to produce a calibrating solution. In the example under consideration assume that the known concentration increment, denoted $c_i$, is 10 parts per billion. This second sample, that is, the calibrating solution, has a concentration of $c_a + c_i$. By proper adjustment of the valves this second sample is supplied to the analyzer cell.

On FIG. 9 the position of the indicator when the concentration of the second sample is being measured is indicated at 205. As illustrated, the meter indicates a concentration of approximately 6.5 parts per billion and a voltage reading of approximately 110 millivolts. This second voltage reading is denoted $E_b$.

From the two voltage readings $E_a$ and $E_b$ and from the known increment $c_i$, the unknown concentration $c_a$ can be determined from the following:

$$E_b - E_a = B \log \frac{(c_a + c_i)}{c_a} \qquad (2)$$

It will be noted that $c_a$ is the only unknown in the above equation. The value B is a constant generally known to a very close degree. When the electrodes are truly operating in accordance with the Nernst equation as discussed above, the value of B will be approximately 59 millivolts at 25° C. The value of B is referred to as the slope constant. Under certain circumstances it may vary and subsequently, a calibration technique will be described for adjusting for a varying value of B.

Having determined the unknown concentration $c_a$, the zero of the meter can be set so that the indicator is at the actual concentration when the unknown sample is being supplied to the analyzer cell. For example, assume that from the values of $E_a$, $E_b$ and $c_i$ described above, it was determined that the actual concentration was 0.5 parts per billion. Then the zero of the meter would be adjusted so that the indicator was at 0.5 when the unknown concentration was being measured.

Alternatively, it will be more convenient to set the zero when the concentration of the second sample is being measured by the system. Since the second sample will normally already be in the analyzer cell it will be convenient to merely adjust the indicator of the meter to read the actual value of this concentration. Note that the actual concentration of the second fluid is $c_a + c_i$ and this value can be determined from Equation (2) above. To summarize, the actual concentration of one of the first sample or the second sample may be determined from Equation (2) above although it will normally be more convenient to determine the actual concentration of the second sample. Thereafter, the indicator on the meter is set to a scale value representing this actual concentration.

The use of a sample liquid having a concentration which is a known concentration increment above the concentration of the first unknown solution is a convenient way of obtaining the zero calibration which will be satisfactory for almost all purposes. While the Equation (2) above can be solved as a step in this calibration procedure it will often be more convenient to use an auxiliary scale, or nomograph. Such an auxiliary scale is shown at 202 in FIG. 9. The auxiliary scale 202 is movable with respect to the fixed scale. It has a reference marking R and scale calibration markings each representing an actual concentration. The distance between the reference mark 204 and any given scale mark is given by $$E_b - E_a = B \log \frac{(c_a + c_i)}{c_a}$$

where the quantities were as previously described.

The procedure in making the calibration with the nomograph is as follows:

When the instrument pointer 201 is indicating the concentration of the first sample, the position of the movable nomogram 202 is adjusted along the instrument scale 203 to make the nomogram reference mark R (204) align with the instrument pointer position 201. It is advisable to have the concentration increment of the second solution at least a little greater in magnitude than the concentration level originally present in the water in reservoir 154. After it is prepared, the second sample is led into the analyzer for measurement. The instrument indicator will move upscale to a new position 205, depending on the particular solution concentration values. Nomograph 202 is provided with a plurality of scale markings 206 calibrated to indicate the actual concentration of the second solution. Thus the concentration of the second solution is obtained by reading the pointer position 205 with respect to the nomogram scale markings 206. If the pointer position 205 as read with respect to the instrument scale 203 does not agree with the indicated nomogram scale value 206, the electrical zero of the instrument is adjusted to make the indicator position read the correct value on the instrument scale 203. The instrument will now be in calibration with respect to the zero constant $E_o$.

The solution remaining in mixing chamber 155 may be saved for use again to repeat the zero check after a period of instrument operation. The correct concentration value of that solution may be stored for recall by means of an erasable memorandum written on chamber 155, or the auxiliary sliding indicator 207, which was previously set at the solution value, may furnish the information.

While the fixed increment method of calibration described above is a very convenient one, another procedure may be used. In this procedure, the sodium ion concentration increment is made a fixed multiple of the first sample concentration as indicated by the analyzer. That is, the concentration of the first sample is measured. Then a second solution is prepared having a concentration such that the sodium ion concentration increment is made a fixed multiple of the starting solution concentration as indicated by the analyzer. It will be appreciated that a nomogram can conveniently be made in this instance to directly indicate the actual concentration of the second sample and to provide an indication of the value at which the meter indicator is to be set when the analyzer cell is measuring the concentration of the second sample.

Calibration of the sodium analyzer for adjustment of both the slope and zero constant will now be described. It is assumed for illustrative purposes that the instrument scale covers three decades of sodium ion concentration from 1 to 1000 parts per billion and that the sample concentration is below 5 ppb. Initially, the "temperature" dial of the pH meter is set at the 25° C reading. By using the mixing chamber as described above, a solution having a sodium ion concentration increment (above sample background) of exactly 500 ppb is prepared. The concentration of this solution can be taken as 500 ppb since the background will not contribute an appreciable effect. A flow of this solution is directed into the analyzer for measurement. When the instrument reading is steady, the "zero-standardization" dial of the pH meter is adjusted to make the recorder readout equal 500, thereby establishing tentative zero-calibration of the instrument. This adjusted reading with magnitude of 500 is termed $R_1$.

Now, valve 152 is switched to the position to shut off chamber 155 and to introduce into the analyzer water from reservoir bottle 154. While as analyzer reading $R_2$ is being obtained on the water from the reservoir 154, the contents of chamber 155 are discharged through valve 161, and a second solution is made up in the chamber 155. After the preliminary rinse, a solution is made up having a total sodium ion concentration of 50 ppb. This is done by making the increment from the micro-pipette correspond to the quantity 50 ppb minus $R_2$. This latter quantity $R_2$ is the approximate sodium ion content (ppb) of the reservoir water. If the reservoir water is of high quality, the instrument indicator may go to the bottom end of the scale. If this should occur, no change is made in the instrument settings and an arbitrary value of 1 ppb is assigned to the quantity $R_2$.

The 50 ppb solution prepared in mixing chamber 155 is now introduced into the analyzer by appropriately changing the setting of valve 152, and the instrument is allowed to continue to operate on this solution until the remainder of the calibration procedure is completed. After a steady reading is obtained, the concentration value, reading $R_3$, is obtained.

The voltage change between readings $R_1$ and $R_3$ correspond to the actual slope constant, because the one-decade concentration change makes the logarithmic term of Equation 2 equal unity. The $R_1$ and $R_3$ readings are now logarithmically converted to values that are proportional to voltage. Table 2 makes this conversion for an array of $R_3$ values, and presents in column 3 the voltage difference values or actual slope constants relative to the theoretical 25° C value. Since the theoretical slope constant is proportional to absolute temperature (°K) the relative relationship between the actual and theoretical slopes may be expressed in terms of a "corresponding temperature." Columns 4 and 5 of Table 2 respectively give Kelvin and Centigrade "corresponding temperatures". It should be understood that a "corresponding temperature" figure different from the original 25° setting of the pH meter may be attributable to an actual operating temperature other than 25° C, a nontheoretical electrode response, or both.

Table 2

| | Data for Adjustment of the Slope Constant | | | |
|---|---|---|---|---|
| (1) Analyzer Reading $R_3$ | (2) Log of $R_3$ | (3) Log of $R_1$ Minus Log of $R_3$ | (4) Corresponding Temperature °K | (5) Corresponding Temperature °C |
| 35 | 1.54407 | 1.15490 | 344.34 | 71.2 |
| 36 | 1.55630 | 1.14267 | 340.70 | 67.5 |
| 37 | 1.56820 | 1.13077 | 337.15 | 64.0 |
| 38 | 1.57978 | 1.11919 | 333.70 | 60.5 |
| 39 | 1.59106 | 1.10791 | 330.33 | 57.2 |
| 40 | 1.60206 | 1.09691 | 327.06 | 53.9 |
| 41 | 1.61278 | 1.08619 | 324.10 | 50.9 |
| 42 | 1.62325 | 1.07572 | 320.79 | 47.6 |
| 43 | 1.63347 | 1.06550 | 317.69 | 44.5 |
| 44 | 1.64345 | 1.05552 | 314.71 | 41.6 |
| 45 | 1.65321 | 1.04576 | 311.80 | 38.6 |
| 46 | 1.66276 | 1.03621 | 308.96 | 35.8 |
| 47 | 1.67210 | 1.02687 | 306.17 | 33.0 |
| 48 | 1.68124 | 1.01773 | 303.45 | 30.3 |
| 49 | 1.69020 | 1.00877 | 300.78 | 27.6 |
| 50 | 1.69897 | 1.00000 | 298.16 | 25.0 |
| 51 | 1.70757 | 0.99140 | 295.59 | 22.4 |
| 52 | 1.71600 | 0.98297 | 293.08 | 19.9 |
| 53 | 1.72428 | 0.97469 | 290.61 | 17.5 |
| 54 | 1.73239 | 0.96658 | 288.20 | 15.0 |
| 55 | 1.74036 | 0.95861 | 285.82 | 12.7 |
| 56 | 1.74819 | 0.95078 | 283.48 | 10.3 |
| 57 | 1.75587 | 0.94310 | 281.19 | 8.0 |
| 58 | 1.76343 | 0.93554 | 278.94 | 5.8 |
| 59 | 1.77085 | 0.92812 | 276.73 | 3.6 |
| 60 | 1.77815 | 0.92082 | 274.55 | 1.4 |
| 61 | 1.78533 | 0.91364 | 272.41 | −0.8 |

With the aid of Table 2, the obtained reading $R_3$ is converted to a temperature value. The temperature dial of the pH meter is set to this value to adjust the span of the meter. This effectively adjusts the system for any variation in the slope constant B.

Then, the zero setting, or "zero-standardization" dial of the pH meter is adjusted to make the reading of the instrument equal exactly to 50 ppb. The system has now been calibrated for both slope and zero. All meters of the type used in ion concentration measurement systems have a span adjustment. One convenient span adjustment which is present in almost all meters is by means of the temperature compensation dial. The span adjustment has been described herein as being made with this temperature compensation dial although it will be appreciated that the same principles may be used in making the calibration with span adjustment in units other than temperature.

Figure 10:
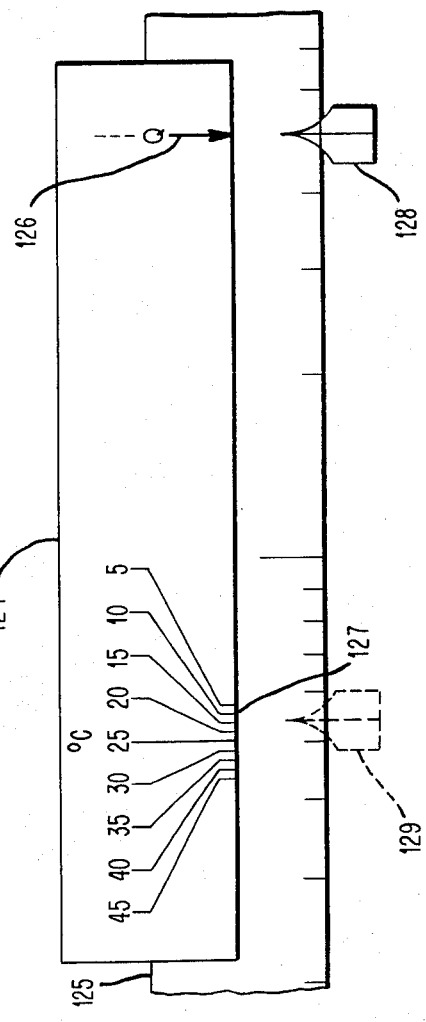
FIG. 10 shows another auxiliary scale.

Instead of using Table 2 above, the information contained therein can be converted to a nomogram which can be used in conjunction with the readings on the meter dial to directly obtain the proper span adjustment. Such a nomogram is shown in FIG. 10.

The nomogram 124 is placed in fixed position on scale 125 with its index Q (126) aligned with the scale value corresponding to 500 ppb. Downscale from Q the nomogram is provided with a plurality of markings 127, each corresponding to a particular setting of the pH meters's "temperature" dial, and these are labeled with temperature designations. The markings 127 are positioned by first locating the 25° C marking at a distance exactly one instrument scale decade downscale from the index Q. The markings corresponding to other temperatures are located by making the distance greater or less than one-decade distance as determined by applying the pertinent factor of Column 3 of Table 2. It may be necessary to interpolate the data to obtain factors corresponding to the particular temperature markings desired.

In the calibration procedure when the analyzer is measuring the 500 ppb solution ($R_1$), the position of the instrument indicator 128 will be adjusted to align with the Q-index 126 of the nomogram. When the 50 ppb solution is introduced, the indicator will assume a new position 129 downscale from $R_1$. The correct setting of the "temperature" dial of the pH meter is obtained by reading the position 129 of the indicator with respect to the nomogram markings 127. After making the correct "temperature" dial setting, adjustment for $E_o$ is carried out as before.

It should be understood in this and the following sections that the principles described may be applied to scale ranges and concentration increment values other than the particular ones used for illustration. The method above described depends on establishing a one-decade ratio between the two solution concentrations, simply because values in Table 2 are based on this ratio. In general, values other than the 50 ppb and 500 ppb of the above example will be used, but the concentration ratio will be kept 10:1. The method conveniently accomplishes this by selecting the magnitude of incremental concentrations to make the background sample concentration $R_2$ appreciably smaller than $R_3$ and very much smaller than $R_1$.

Figure 11:
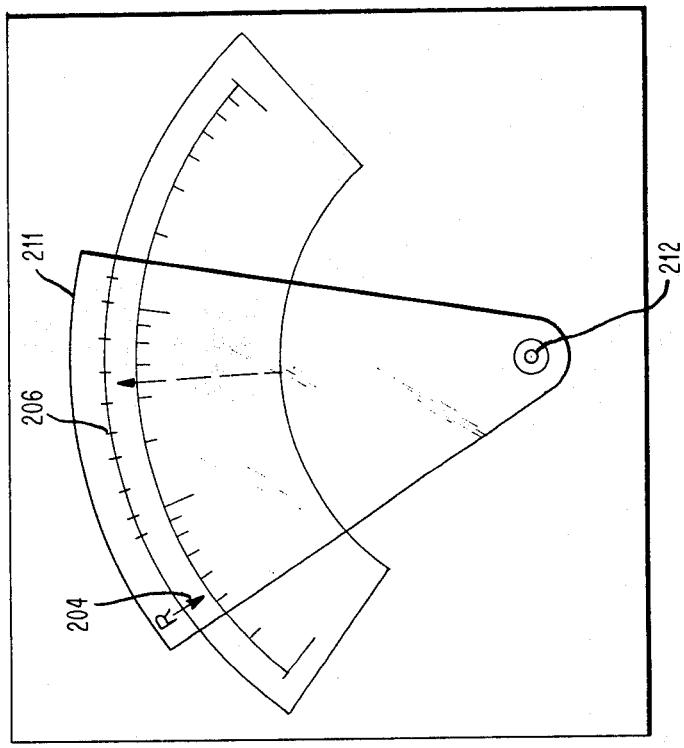
FIG. 11 shows another auxiliary scale.

An alternative form of nomogram for the constant increment procedure and for use with a deflection indicator of the ammeter type is illustrated in FIG. 11. The nomogram 211 of transparent material is made rotatable around the pointer pivot point 212, thereby allowing the angular position of the nomogram to be adjusted. As before, the nomogram has an R reference mark 204 and a specially calibrated scale comprising a plurality of markings 206. The procedure in operating the nomogram of FIG. 11 is quite analogous to that which has already been described for the nomogram of FIG. 9, and need not be described again.

The way in which the special scale calibration 206 of the nomograms of FIGS. 9 and 11 is obtained will now be described, along with an explanation of the operating principle. The fundamental instrument equation is repeated for convenience:

$$\Delta E = E_b - E_a = B \log \frac{(c_a + c_i)}{c_a}$$

where the symbols are defined as before. Rearranging the above gives:

$$\frac{\Delta E}{B} = \log (c_a + c_i) - \log c_a$$

Application of this Equation to the case where the fixed concentration increment $c_i$ is 10 ppb is given in Table 3.

Table 3

| 1. First Sample Concentration in ppb $c_a$ | 2. Second Sample Concentration $(c_a + c_i)$ | 3. log $c_a$ | 4. log $(c_a + c_i)$ | 5. Indicator Displacement in Decades $\Delta E/B$ |
|---|---|---|---|---|
| 0.10 | 10.10 | −1.0000 | 1.0043 | 2.0043 |
| 0.15 | 10.15 | −0.8239 | 1.0065 | 1.8304 |
| 0.20 | 10.20 | −0.6980 | 1.0086 | 1.7066 |
| 0.25 | 10.25 | −0.6021 | 1.0107 | 1.6128 |
| 0.30 | 10.30 | −0.5229 | 1.0128 | 1.5357 |
| 0.40 | 10.40 | −0.3979 | 1.0170 | 1.4149 |
| 0.50 | 10.50 | −0.3010 | 1.0212 | 1.3222 |
| 0.60 | 10.60 | −0.2218 | 1.0253 | 1.2471 |
| 0.70 | 10.70 | −0.1549 | 1.0294 | 1.1843 |
| 0.80 | 10.80 | −0.0969 | 1.0334 | 1.1303 |
| 0.90 | 10.90 | −0.0458 | 1.0374 | 1.0832 |
| 1.0 | 11.0 | 0 | 1.0414 | 1.0414 |
| 1.5 | 11.5 | +0.1761 | 1.0607 | 0.8846 |
| 2.0 | 12.0 | 0.3010 | 1.0792 | 0.7782 |
| 2.5 | 12.5 | 0.3979 | 1.0969 | 0.6990 |
| 3.0 | 13.0 | 0.4771 | 1.1139 | 0.6368 |
| 4.0 | 14.0 | 0.6020 | 1.1461 | 0.5441 |
| 5.0 | 15.0 | 0.6990 | 1.1761 | 0.4771 |
| 6.0 | 16.0 | 0.7782 | 1.2041 | 0.4259 |
| 7.0 | 17.0 | 0.8451 | 1.2304 | 0.3853 |
| 8.0 | 18.0 | 0.9031 | 1.2553 | 0.3522 |
| 9.0 | 19.0 | 0.9542 | 1.2788 | 0.3246 |
| 10.0 | 20.0 | 1.0000 | 1.3010 | 0.3010 |

The first column gives an array of starting solution concentrations ranging from 0.1 to 10.0 ppb. The second column shows values of concentration of the second solution corresponding to the values of the first column. The last column gives values of upscale displacement, expressed as the number of scale decades, for corresponding values of initial concentration listed in the first column. The nomograms of FIGS. 9 and 11 are constructed by measuring upscale from point R the distance or angular displacement values of ΔE/B, corresponding to each designated value of the concentration of the second solution.

While particular embodiments of the invention have been shown and described, it will, of course, be understood that various modifications may be made without departing from the principles of the invention. The appended claims are, therefore, intended to cover any such modification within the true spirit and scope of the invention.

We claim:

1. A method of calibrating a system for measuring ion concentration including an analyzer cell having an electrode which produces a voltage representing the concentration of selected ions in contact with said electrode and a meter having an indicator which moves over a meter scale in accordance with the voltage on said electrode and an auxiliary scale on said meter movable with respect to said fixed scale comprising:

supplying to said analyzer cell a first sample having unknown concentration $c_a$, moving said auxiliary scale to a position such that a reference mark on said auxiliary scale corresponds with the position of said indicator when said first sample is in said analyzer cell, supplying a second sample liquid having a concentration which is a known increment $c_i$ above the concentration $c_a$, determining from said auxiliary scale the actual concentration of said second sample as indicated by the position of said indicator with respect to calibration markings on said second scale, and adjusting the zero adjustment of said meter so that said indicator reads said value of actual concentration on said meter scale when said second sample is in said analyzer cell.

2. In a system for measuring ion concentration in a sample liquid, said system including an analyzer cell having an electrode which produces a voltage representing the concentration of ions in contact with said electrode, and a meter having an indicator which moves over a meter scale in accordance with the voltage on said electrode, calibration apparatus comprising:

means for supplying to said analyzer cell a first sample having unknown concentrations $c_a$ and for supplying a second sample liquid having a concentration which is a known concentration increment $c_i$ above the concentration $c_a$, and an auxiliary scale on said meter movable with respect to said fixed scale, said auxiliary scale having:

a reference marking, scale calibration markings representing concentration, the distance between the reference marking and any scale marking being given by $$E_b - E_a = B \log \frac{(c_a + c_i)}{c_a}$$

where B is a known constant and $E_a$ is the voltage on the electrode when said first solution is in contact with it, $E_b$ is the voltage on said electrode when said second voltage is in contact with it, said auxiliary scale being movable with respect to said fixed scale so that said reference mark is aligned with said indicator when said first sample liquid is supplied to said analyzer.

* * * * *